US009949626B2

(12) United States Patent
Komiya (10) Patent No.: US 9,949,626 B2
(45) Date of Patent: Apr. 24, 2018

(54) ENDOSCOPE REPROCESSOR (71) Applicant: OLYMPUS CORPORATION, Tokyo (JP)

(72) Inventor: Takaaki Komiya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/409,637

(22) Filed: Jan. 19, 2017

(65) Prior Publication Data

US 2017/0128988 A1     May 11, 2017

Related U.S. Application Data (63) Continuation of application No. PCT/JP2016/061569, filed on Apr. 8, 2016.

(30) Foreign Application Priority Data

May 27, 2015 (JP) ................. 2015-107809

(51) Int. Cl.
| *A61B 1/12* | (2006.01) |
| *B08B 9/032* | (2006.01) |
| *B08B 9/023* | (2006.01) |
| *B08B 3/10* | (2006.01) |
| *G02B 27/00* | (2006.01) |

(52) U.S. Cl.
CPC ............. *A61B 1/123* (2013.01); *B08B 3/102* (2013.01); *B08B 9/023* (2013.01); *B08B 9/0325* (2013.01); *G02B 27/0006* (2013.01)

(58) Field of Classification Search
CPC ..................................................... A61B 1/123
See application file for complete search history.

(56) References Cited

U.S. PATENT DOCUMENTS

| 2005/0000553 A1* | 1/2005 | Noguchi ............ A61B 1/00144 134/84 |
| 2010/0004510 A1* | 1/2010 | Kuroshima ............ A61B 1/012 600/158 |
| 2012/0031506 A1 | 2/2012 | Komiya et al. |

FOREIGN PATENT DOCUMENTS

| JP | S58-192525 A | 11/1983 |
| JP | 2004-135946 A | 5/2004 |

(Continued)

OTHER PUBLICATIONS

International Search Report dated Jul. 5, 2016 issued in PCT/JP2016/061569.

*Primary Examiner* — Spencer E Bell
(74) *Attorney, Agent, or Firm* — Scully, Scott, Murphy & Presser, P.C.

(57) ABSTRACT

An endoscope reprocessor includes a control section and a flow liquid pump. The control section controls a plurality of electromagnetic valves to set a first drive state, in which the control section puts a first cleaning tube connected to a suction pipe sleeve of an endoscope into a sealed state, the control section puts a second cleaning tube connected to a forceps plug pipe sleeve of a forceps plug of the endoscope into an unsealed state, the control section controls an electromagnetic valve configured to switch a state of a connector plugging a suction cylinder of the endoscope to put the connector into a sealed state, the control section sets a state in which a fluid is supplied from the flow liquid pump to the first cleaning tube, and the control section halts supply of the fluid from the flow liquid pump to the second cleaning tube.

9 Claims, 5 Drawing Sheets

(56) References Cited

FOREIGN PATENT DOCUMENTS

| JP | 2012-050817 A | 3/2012 |
|---|---|---|
| WO | WO 2012/017720 A1 | 2/2012 |

* cited by examiner

ENDOSCOPE REPROCESSOR

CROSS REFERENCE TO RELATED APPLICATION

This application is a continuation application of PCT/JP2016/061569 filed on Apr. 8, 2016 and claims benefit of Japanese Application No. 2015-107809 filed in Japan on May 27, 2015, the entire contents of which are incorporated herein by this reference.

BACKGROUND OF THE INVENTION

1. Field of the Invention

The present invention relates to an endoscope reprocessor.

2. Description of the Related Art

Conventionally, an endoscope, which includes an elongated insertion portion, has been widely used for various inspections and various therapies inside of a body. Various conduits for air feeding, water feeding, sucking, and the like are provided inside of the endoscope. After the use of the endoscope, cleaning and the like of not only an outer surface of the endoscope, but also the inside of various conduits are performed.

The endoscope is cleaned and disinfected by using, for example, a dedicated endoscope cleaning/disinfecting apparatus. The endoscope is immersed in a treatment tank, and a connection tube for supplying a cleaning liquid or the like to pipe sleeves or the like of various conduits of the endoscope is connected to supply the cleaning liquid or the like through the connection tube to perform cleaning and the like. The endoscope cleaning/disinfecting apparatus also measures an amount of flow or a pressure of a liquid flowing through the connection tube to detect clogging of various conduits.

Furthermore, Japanese Patent Application Laid-Open Publication No. 2004-135946 proposes an endoscope cleaning/disinfecting apparatus that can put a connection part of a cleaning tube and a pipe sleeve into a sealed state and an unsealed state to allow securing washability of a pipe sleeve part and detecting clogging of a conduit.

SUMMARY OF THE INVENTION

An aspect of the present invention provides an endoscope reprocessor including: a first attachment portion connected to a suction pipe sleeve of an endoscope, the first attachment portion configured to attach a first cleaning tube capable of switching a first off-state in which an entire amount of a fluid is introduced into the suction pipe sleeve and a first on-state in which the fluid is introduced into the suction pipe sleeve and a first predetermined amount of the fluid is leaked to an outer circumference of the suction pipe sleeve; a first switch portion configured to switch the first on-state and the first off-state of the first cleaning tube; a first fluid supply portion configured to supply the fluid from the first attachment portion to the suction pipe sleeve through the first cleaning tube; a second attachment portion connected to a forceps plug pipe sleeve of the endoscope, the second attachment portion configured to attach a second cleaning tube capable of switching a second off-state in which an entire amount of the fluid is introduced into the forceps plug pipe sleeve and a second on-state in which the fluid is introduced into the forceps plug pipe sleeve and a second predetermined amount of the fluid is leaked to an outer circumference of the forceps plug pipe sleeve; a second switch portion configured to switch the second on-state and the second off-state of the second cleaning tube; a second fluid supply portion configured to supply the fluid from the second attachment portion to the forceps plug pipe sleeve through the second cleaning tube; a third switch portion configured to switch a third off-state and a third-on state of a connector plugging a suction cylinder of the endoscope, wherein the fluid is not leaked from the suction cylinder in the third off-state, and a third predetermined amount of the fluid is leaked from the suction cylinder in the third on-state; and a control section configured to control the first switch portion, the second switch portion, the third switch portion, the first fluid supply portion, and the second fluid supply portion to set a first drive state, in which the control section controls the first switch portion to put the first cleaning tube into the first off-state, the control section controls the second switch portion to put the second cleaning tube into the second on-state, the control section controls the third switch portion to put the connector into the third off-state, the control section sets a state in which the fluid is supplied from the first fluid supply portion to the first cleaning tube, and the control section sets a state in which supply of the fluid from the second fluid supply portion to the second cleaning tube is halted.

DETAILED DESCRIPTION OF THE PREFERRED EMBODIMENT(S)

Hereinafter, an embodiment of the present invention will be described with reference to the drawings.

Figure 1:
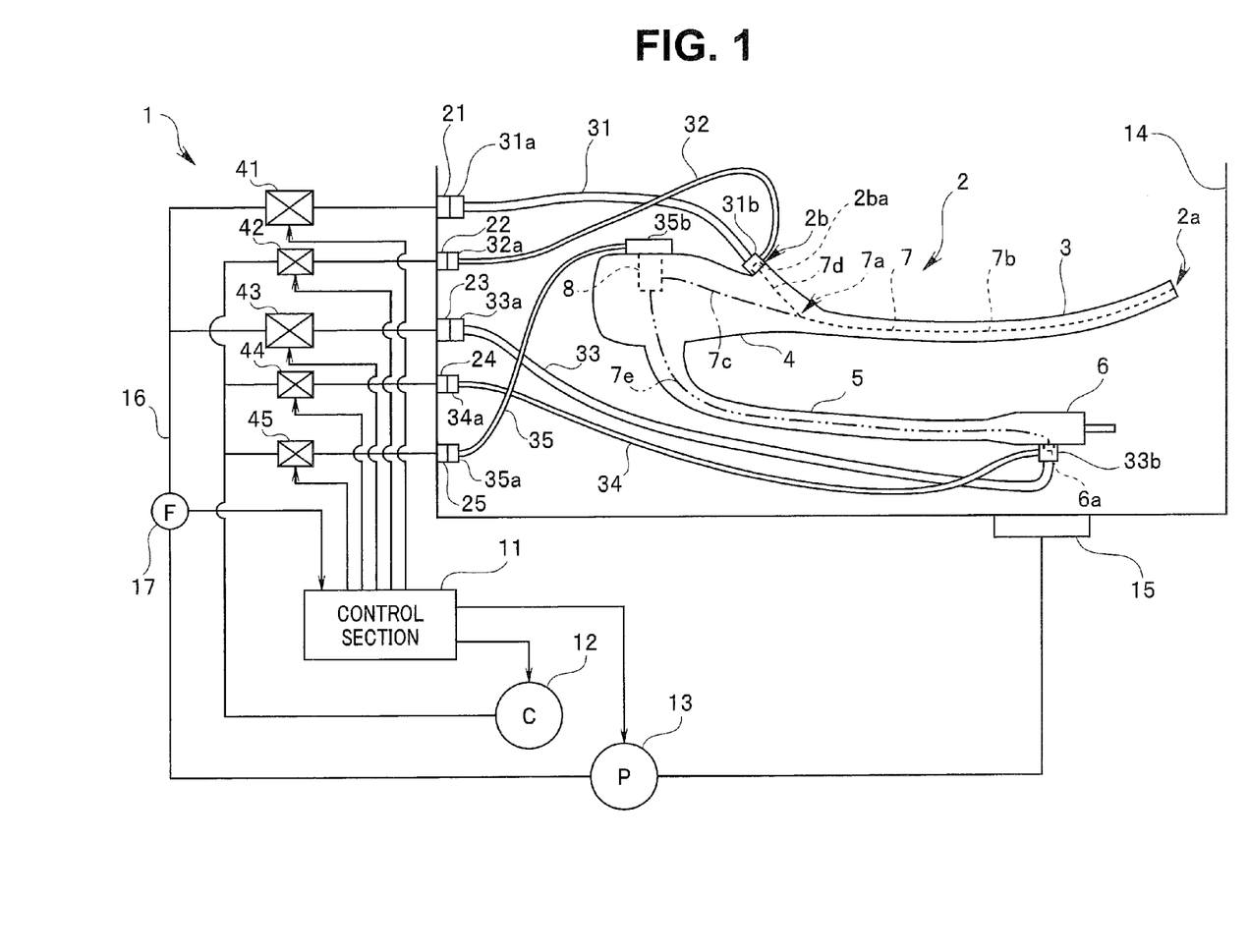
FIG. 1 is a schematic configuration diagram showing a configuration of an endoscope and an endoscope reprocessor according to an embodiment of the present invention.

FIG. 1 is a schematic configuration diagram showing a configuration of an endoscope and an endoscope reprocessor according to the present embodiment.

(Configuration of Endoscope)

An endoscope 2 includes: an elongated insertion portion 3; an operation portion 4 to which a proximal end portion of the insertion portion 3 is connected; a cable 5 extended from the operation portion 4; and a connector portion 6 provided on a distal end portion of the cable 5.

A treatment instrument insertion channel 7 (indicated by a dotted line) is provided in the insertion portion 3 of the endoscope 2. One end of the treatment instrument insertion channel 7 communicates with an opening 2a of a distal end portion of the insertion portion 3, and the other end communicates with a treatment instrument insertion port 2b provided near the operation portion 4. A forceps plug pipe sleeve 2ba is provided on the treatment instrument insertion port 2b.

A suction cylinder 8 configured to attach a suction button (not shown) is provided on the operation portion 4. A suction pipe sleeve 6a provided on the connector portion 6 and the suction cylinder 8 communicate with each other through a suction conduit 7e.

The treatment instrument insertion channel 7 includes: a distal end side conduit 7b connected to the opening 2a; and a proximal end side conduit 7d connected to the treatment instrument insertion port 2b. A branch portion 7a is arranged between the distal end side conduit 7b and the proximal end side conduit 7d.

A connection conduit 7c (indicated by an alternate long and short dash line), one end of which is connected to the suction cylinder 8 and the other end of which is connected to the branch portion 7a, is arranged inside of the insertion portion 3 on a proximal end side.

The suction conduit 7e (indicated by an alternate long and two short dashes line), one end of which is connected to the suction pipe sleeve 6a and the other end of which is connected to the suction cylinder 8, is arranged inside of the cable 5.

The treatment instrument insertion channel 7 (7b, 7d) and the connection conduit 7c communicate with each other, with the branch portion 7a as a contact point. The connection conduit 7c and the suction conduit 7e communicate with each other, with the suction cylinder 8 as a contact point.

In the world, an endoscope in which an inner diameter of the distal end side conduit 7b is smaller than that of the connection conduit 7c, the proximal end side conduit 7d, and the suction conduit 7e also exists.

A user of the endoscope 2 can operate the suction button (not shown) installed on the suction cylinder 8 to perform suction operation from the opening 2a of the distal end portion of the insertion portion 3.

Note that the endoscope 2 includes a bending portion (not shown) on the distal end portion of the insertion portion 3, and a bending knob for bending operation of the bending portion, a freeze button for shooting, and the like are provided on the operation portion 4. However, the bending portion and the like are not illustrated here, and the description is also omitted.

(Configuration of Endoscope Reprocessor 1)

Note that an endoscope reprocessor 1 here is an endoscope cleaning/disinfecting apparatus configured to execute reprocessing of a contaminated endoscope or endoscope accessories. However, the endoscope reprocessor 1 may be an apparatus configured to execute one of or a combination of rinsing the endoscope 2 by water or volatile fluid, cleaning stains such as organic matters, disinfecting and eliminating predetermined microorganisms, and killing or sterilizing the predetermined microorganisms.

The endoscope reprocessor 1 includes a control section 11, an air compressor 12, and a flow liquid pump 13. The control section 11 includes a central processing unit (hereinafter, called CPU), a ROM, a RAM, and the like. The endoscope reprocessor 1 includes an operation panel not shown. When the user operates the operation panel, the control section 11 reads a predetermined program from the ROM and executes the program according to an inputted instruction to realize a function according to the instruction of the user.

The endoscope reprocessor 1 includes a treatment tank 14, and the endoscope comes into contact with a liquid in the treatment tank 14. A circulating liquid suction port 15 is provided on a bottom surface of the treatment tank 14. Although the treatment tank 14 may have a depth that allows the entire endoscope 2 to immerse when a process of immersing the endoscope 2 in the liquid is executed, the present invention is not limited to this. The endoscope 2 may be immersed in the liquid or may be subjected to a shower process, or a fluid may be just introduced into a conduit.

A plurality of connection connectors 21 to 25 are further provided near the treatment tank 14. Note that although FIG. 1 illustrates the plurality of connection connectors 21 to 25 as if the plurality of connection connectors 21 to 25 are provided on a sidewall of the treatment tank 14 for the simplification of the illustration, the plurality of connection connectors 21 to 25 are arranged on a peripheral portion of an upper surface side edge portion of the treatment tank 14.

A second cleaning tube 31 is connected to the connection connector 21. A connector 31a at one end of the second cleaning tube 31 may be able to be attached to and detached from the connection connector 21 or may be integrated. A connector 31b at the other end of the second cleaning tube 31 is detachably connected to the forceps plug pipe sleeve 2ba of the treatment instrument insertion port 2b.

The connector 31b is a connector that can put a part between the connector 31b and the forceps plug pipe sleeve 2ba of the connected treatment instrument insertion port 2b into one of a sealed state and an unsealed state.

When a fluid is introduced from the second cleaning tube 31 in the sealed state, the entire amount of the fluid is introduced into the forceps plug pipe sleeve 2ba. This will be called an off-state in the present invention. The fluid can be introduced into the endoscope conduit at a high speed of flow in the off-state.

When the fluid is introduced from the second cleaning tube 31 in the unsealed state, part of the fluid is introduced into the forceps plug pipe sleeve 2ba, and the rest leaks to the surroundings of a forceps plug. This will be called an on-state in the present invention. In the on-state, both of the endoscope conduit and the surroundings of the forceps plug can be cleaned or disinfected.

The connector 31b has a structure similar to, for example, the connector disclosed in Japanese Patent Application Laid-Open Publication No. 2004-135946 and includes: a sealing member; and a sealing member biasing member configured to apply external force to the sealing member to allow control in a sealed state in which a passage between the forceps plug pipe sleeve 2ba of the treatment instrument insertion port 2b and the connector 31b is sealed and a released state in which the sealed state is released.

The second cleaning tube 31 is connected to the forceps plug pipe sleeve 2ba that is a forceps plug pipe sleeve of the endoscope 2. The second cleaning tube 31 is a tube that can make a switch between an off-state in which the entire fluid is introduced into the forceps plug pipe sleeve 2ba and an on-state in which the fluid is introduced into the forceps plug pipe sleeve 2ba and a predetermined amount of the fluid is leaked to an outer circumference of the forceps plug pipe sleeve 2ba. The connection connector 21 configures an attachment portion configured to attach the second cleaning tube 31.

An air supply tube 32 is connected to the connection connector 22. A connector 32a at one end of the air supply tube 32 can be connected to the connection connector 22. The other end of the air supply tube 32 is connected to an air supply port of the connector 31b.

When air is supplied from the air supply tube 32 to the connector 31b, a sealing member inside of the connector 31b expands and comes into close contact with an outer circumference portion of the forceps plug pipe sleeve 2ba of the treatment instrument insertion port 2b. The passage between the forceps plug pipe sleeve 2ba of the treatment instrument insertion port 2b and the connector 31b enters the sealed state.

When the supply of the air from the air supply tube 32 to the connector 31b is halted, the sealing member inside of the connector 31b contracts, and the sealing member does not come into close contact with the outer circumference portion of the forceps plug pipe sleeve 2ba of the treatment instrument insertion port 2b. The passage between the forceps plug pipe sleeve 2ba of the treatment instrument insertion port 2b and the connector 31b enters the unsealed state.

That is, the sealed state is a state in which the liquid does not leak from between the connector 31b and the forceps plug pipe sleeve 2ba, and the unsealed state is a state in which the liquid leaks from between the connector 31b and the forceps plug pipe sleeve 2ba. In the sealed state, the entire amount of the liquid flowing through the second cleaning tube 31 is introduced into the forceps plug pipe sleeve 2ba from the connector 31b without a leak. In the unsealed state, a predetermined amount of the liquid flowing through the second cleaning tube 31 leaks, and the rest of the liquid is introduced into the forceps plug pipe sleeve 2ba from the connector 31b.

A first cleaning tube 33 is connected to the connection connector 23. A connector 33a at one end of the first cleaning tube 33 can be connected to the connection connector 23. A connector 33b at the other end of the first cleaning tube 33 is detachably connected to the suction pipe sleeve 6a of the connector portion 6.

The connector 33b has a configuration similar to the connector 31b and is a connector that can put a part between the connector 33b and the connected suction pipe sleeve 6a of the connector portion 6 into one of the sealed state and unsealed state.

That is, the first cleaning tube 33 is a tube connected to the suction pipe sleeve 6a of the endoscope 2 and capable of making a switch between the off-state in which the entire amount of the fluid is introduced into the suction pipe sleeve and the on-state in which the fluid is introduced into the suction pipe sleeve 6a and a predetermined amount of the fluid is leaked to an outer circumference of the suction pipe sleeve 6a. The connection connector 23 configures an attachment portion for attaching the first cleaning tube 33.

An air supply tube 34 is connected to the connection connector 24. A connector 34a at one end of the air supply tube 34 can be connected to the connection connector 24. The other end of the air supply tube 34 is connected to an air supply port of the connector 33b.

When air is supplied from the air supply tube 34 to the connector 33b, a sealing member inside of the connector 33b expands and comes into close contact with an outer circumference portion of the suction pipe sleeve 6a of the connector portion 6. A passage between the suction pipe sleeve 6a of the connector portion 6 and the connector 33b enters the sealed state.

When the supply of the air from the air supply tube 34 to the connector 33b is halted, the sealing member inside of the connector 33b contracts, and the sealing member does not come into close contact with the outer circumference portion of the suction pipe sleeve 6a of the connector portion 6. The passage between the suction pipe sleeve 6a of the connector portion 6 and the connector 31b enters the unsealed state.

An air supply tube 35 is connected to the connection connector 25. A connector 35a at one end of the air supply tube 35 can be connected to the connection connector 23. The other end of the air supply tube 35 is a connector 35b that can be installed on the suction cylinder 8. The connector 35b is a connector for plugging the suction cylinder 8.

The connector 35b has a configuration similar to the connector 31b and is a connector that can put a part between the connector 35b and the connected suction cylinder 8 into one of the sealed state and the unsealed state. In the sealed state, the connector 35b is in a state in which the liquid is not ejected from between the suction cylinder 8 and the connector 35b, that is, a state in which the liquid does not leak. In the unsealed state, the connector 35b enters a state in which the liquid can be ejected from between the suction cylinder 8 and the connector 35b, that is, a state in which leakage of the liquid is possible.

The connection connectors 21 to 25 are connected to electromagnetic valves 41 to 45, respectively. The connection connectors 21 and 23 are connected to the flow liquid pump 13 through the electromagnetic valves 41 and 43, respectively.

Therefore, the flow liquid pump 13 and the electromagnetic valve 41 configure a fluid supply portion configured to supply the fluid from the connection connector 21 to the forceps plug pipe sleeve 2ba through the second cleaning tube 31. The flow liquid pump 13 and the electromagnetic valve 43 configure a fluid supply portion configured to supply the fluid from the connection connector 23 to the suction pipe sleeve 6a through the first cleaning tube 33.

Note that although one flow liquid pump 13 is connected to the connection connectors 21 and 23 here, a separate flow liquid pump may be connected to each of the connection connectors 21 and 23.

The flow liquid pump 13 is further connected to a circulating liquid suction port 15 on the bottom surface of the treatment tank 14 that is a treatment tank. However, the present invention is not limited to this, and for example, the flow liquid pump 13 may be connected to a tank reserving water or a medicinal solution.

The connection connectors 22, 24, and 25 are connected to the air compressor 12 through the electromagnetic valves 42, 44, and 45, respectively.

The control section 11 is connected to the air compressor 12 and the flow liquid pump 13 and can control start and halt operation. The flow liquid pump 13 is connected to the two electromagnetic valves 41 and 43 through a conduit 16, and a flow amount sensor 17 is provided on the conduit 16. The flow amount sensor 17 is connected to the control section 11 and outputs a detected flow amount value, that is, a fluid feeding amount, to the control section 11. The flow amount sensor 17 is a detector configured to detect clogging of the conduit 16 as described later and is a flow amount sensor configured to measure an amount of flow of the fluid supplied from the flow liquid pump 13.

The control section 11 is connected to the electromagnetic valves 41 to 45 and outputs on/off signals for controlling open and close operation of the respective electromagnetic valves 41 to 45. The respective electromagnetic valves 41 to 45 enter a closed state according to the on-signal and enter an open state according to the off-signal.

The electromagnetic valve 41 configures a switch portion configured to switch a state in which the fluid is introduced from the flow liquid pump 13 to the second cleaning tube 31 and a state in which the fluid is not introduced from the flow liquid pump 13 to the second cleaning tube 31. The control section 11 controls the electromagnetic valve 41 to set a state in which the supply of the fluid from the flow liquid pump 13 to the second cleaning tube 31 is halted.

The electromagnetic valve 42 configures a switch portion configured to switch the on-state and the off-state of the second cleaning tube 31.

The electromagnetic valve 43 configures a switch portion configured to switch a state in which the fluid is introduced from the flow liquid pump 13 to the first cleaning tube 33 and a state in which the fluid is not introduced from the flow liquid pump 13 to the first cleaning tube 33. The control section 11 controls the electromagnetic valve 43 to set a state in which the fluid is supplied from the flow liquid pump 13 to the first cleaning tube 33.

The electromagnetic valve 44 configures a switch portion configured to switch the on-state and the off-state of the first cleaning tube 33.

The electromagnetic valve 45 configures a switch portion configured to switch between the off-state and the on-state of the connector 35b plugging the suction cylinder 8 of the endoscope 2, wherein the fluid is not leaked from the suction cylinder 8 in the off-state, and a predetermined amount of the fluid is leaked from the suction cylinder 8 in the on-state.

As described, the control section 11 includes the CPU and reads programs stored in the ROM to execute various processes.

(Action)

Figure 2:
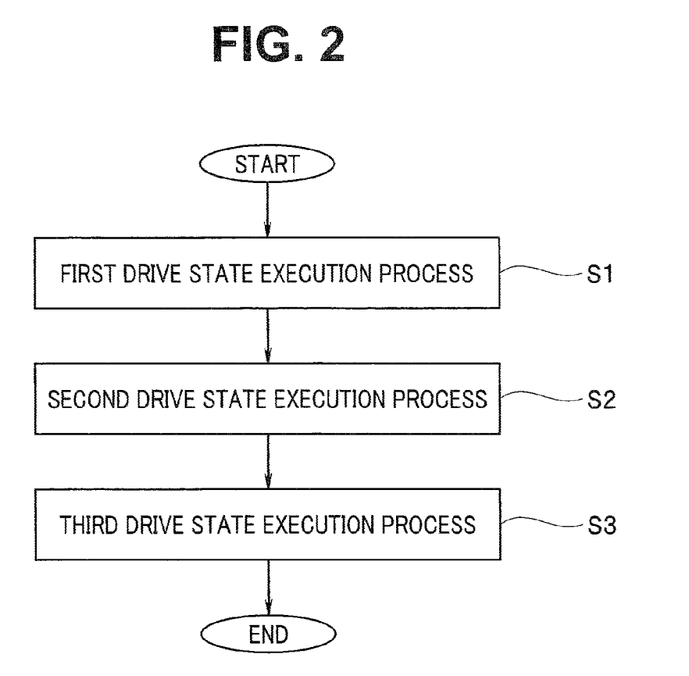
FIG. 2 is a flowchart showing an example of a flow of reprocessing of an endoscope reprocessor 1 according to the embodiment of the present invention.

FIG. 2 is a flowchart showing an example of a flow of reprocessing of the endoscope reprocessor 1. The reprocessing here can be any of a rinsing process, a cleaning process, and a disinfecting process.

One of the processes may be individually executed, or a combination of the processes may be executed. It is preferable to apply the present invention to the cleaning process, because an effect of removing stains of the endoscope conduit is high. The CPU of the control section 11 reads and executes a program written in the ROM to control the starting and halting of the air compressor 12 and the flow liquid pump 13 and the opening and closing of the respective electromagnetic valves 41 to 45 to execute the cleaning process.

Before the execution of the cleaning process, the user that is a worker who performs the cleaning sets the endoscope 2 in the treatment tank 14 of the endoscope reprocessor 1 as shown in FIG. 1 and connects the second cleaning tube 31, the first cleaning tube 33, and the three air supply tubes 32, 34, and 35 to the endoscope 2.

The user gives an execution instruction of the cleaning process to the operation panel not shown to start the cleaning process.

First, after reservation of water (liquid) in the treatment tank 14 from a faucet not shown, input of a detergent, and creation of a cleaning liquid, the control section 11 starts the air compressor 12 and the flow liquid pump 13 to execute the process of FIG. 2.

The control section 11 executes a first drive state execution process (S1), executes a second drive state execution process (S2) after the first drive state execution process, and executes a third drive state execution process (S3) after the second drive state execution process. Hereinafter, the process of the execution of each drive state will be described.

(First Drive State Execution Process: S1)

Figure 3:
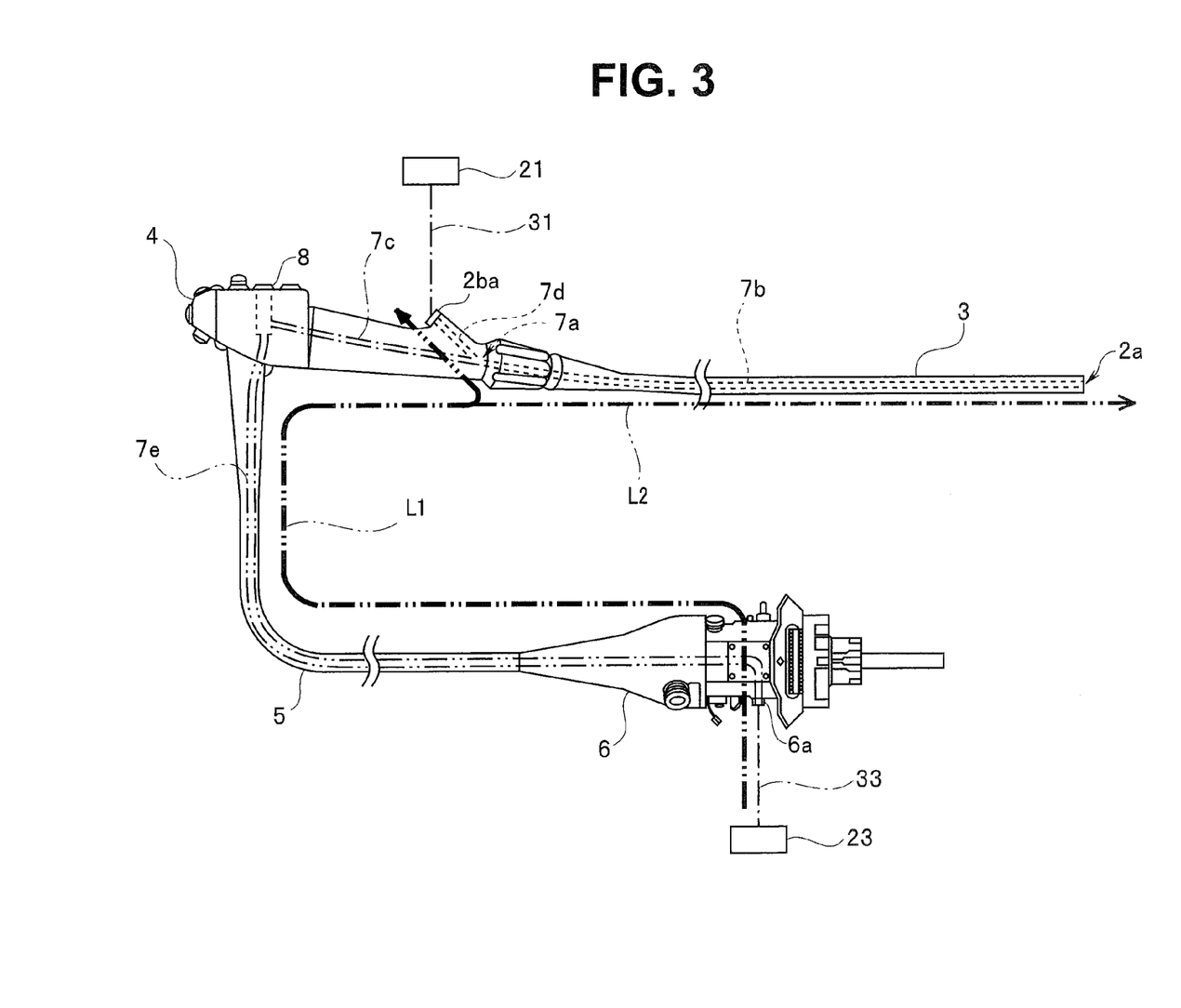
FIG. 3 is a diagram for describing a flow of a liquid in a first drive state execution process according to the embodiment of the present invention.

The first drive state execution process is a process of cleaning the conduit from the suction pipe sleeve 6a to the forceps plug pipe sleeve 2ba of the treatment instrument insertion port 2b, cleaning the forceps plug pipe sleeve 2ba of the treatment instrument insertion port 2b, and detecting clogging of the connection conduit 7c, the proximal end side conduit 7d, and the suction conduit 7e.

The control section 11 executes the first drive state by controlling the electromagnetic valves 41 to 45 to turn on the electromagnetic valve 41, turn on the electromagnetic valve 42, turn off the electromagnetic valve 43, turn off the electromagnetic valve 44, and turn off the electromagnetic valve 45.

FIG. 3 is a diagram for describing a flow of the liquid in the first drive state execution process.

In the first drive state, the control section 11 controls the electromagnetic valves 41 to 45 as described above. As a result, the liquid is supplied into the suction conduit 7e from the suction pipe sleeve 6a, and the liquid is ejected from the forceps plug pipe sleeve 2ba of the treatment instrument insertion port 2b and the opening 2a of the distal end portion of the insertion portion 3 as shown in FIG. 3.

In the first drive state, the electromagnetic valve 41 is turned on and closed, and the liquid from the flow liquid pump 13 is not supplied to the second cleaning tube 31. The electromagnetic valve 43 is turned off and opened, and the liquid from the flow liquid pump 13 is supplied to the suction pipe sleeve 6a of the connector portion 6 through the first cleaning tube 33.

In the first drive state, the electromagnetic valve 42 is turned on and closed, and the passage between the forceps plug pipe sleeve 2ba of the treatment instrument insertion port 2b and the connector 31b enters the unsealed state. The electromagnetic valve 44 is turned off and opened, and the passage between the suction pipe sleeve 6a and the connector 33b enters the sealed state. The electromagnetic valve 45 is turned off and opened, and the part between the suction cylinder 8 and the connector 35b enters the sealed state in which the liquid is not leaked.

That is, the control section 11 controls the electromagnetic valves 41 to 45 and the flow liquid pump 13 to set the first drive state, in which the control section 11 controls the electromagnetic valve 44 to put the first cleaning tube 33 into the off-state, the control section 11 controls the electromagnetic valve 42 to put the second cleaning tube 31 into the on-state, the control section 11 controls the electromagnetic valve 45 to put the connector 35b into the off-state, the control section 11 sets the state in which the fluid is supplied from the flow liquid pump 13 to the first cleaning tube 33 through the electromagnetic valve 43, and the control section 11 sets the state in which the supply of the fluid from the flow liquid pump 13 to the second cleaning tube 31 through the electromagnetic valve 41 is halted.

As a result, the passage between the suction pipe sleeve 6a and the connector 33b enters the sealed state, and the entire amount of the liquid from the flow liquid pump 13 is poured into the suction conduit 7e in the first drive state. The suction cylinder 8 is in the sealed state, and the entire amount of the liquid poured into the suction conduit 7e is poured into the connection conduit 7c. The liquid poured into the connection conduit 7c is branched at the branch portion 7a and is poured into the distal end side conduit 7b and the proximal end side conduit 7d.

The liquid poured into the distal end side conduit 7b is ejected from the opening 2a of the distal end portion of the insertion portion 3, and the liquid poured into the proximal end side conduit 7d leaks out from between the forceps plug pipe sleeve 2ba and the connector 31b, because the passage between the forceps plug pipe sleeve 2ba of the treatment instrument insertion port 2b and the connector 31b is in the unsealed state.

In the first drive state, the liquid poured into the suction conduit 7e from the suction pipe sleeve 6a flows in the suction conduit 7e, the connection conduit 7c, the proximal end side conduit 7d, and the distal end side conduit 7b as indicated by an alternate long and two short dashes line in FIG. 3, and the amount of flow in the proximal end side conduit 7d is greater than the amount of flow in the distal end side conduit 7b, because the inner diameter of the distal end side conduit 7b is small. FIG. 3 illustrates that the amount of a flow L1 indicated by a thick alternate long and two short dashes line is greater than the amount of a flow L2 of the liquid indicated by a thin alternate long and two short dashes line.

Therefore, the connector 35b is in the sealed state, and the forceps plug pipe sleeve 2ba is in the unsealed state in the first drive state. Thus, the liquid poured into the suction conduit 7e from the suction pipe sleeve 6a comes out not only from the distal end side conduit 7b, but also from the proximal end side conduit 7d. As a result, the amount of flow and the speed of flow of the liquid passing through the suction conduit 7e can be maintained at a target amount and speed.

The forceps plug pipe sleeve 2ba of the treatment instrument insertion port 2b is in the unsealed state, and the liquid leaks out at the forceps plug pipe sleeve 2ba. Therefore, the forceps plug pipe sleeve 2ba is also cleaned.

Furthermore, when one of the connection conduit 7c, the proximal end side conduit 7d, and the suction conduit 7e is clogged by foreign matters, the detection value of the flow amount sensor 17, that is, the fluid feeding amount, becomes small, and the clogging can also be detected.

As described, the inside of the connection conduit 7c, the proximal end side conduit 7d, and the suction conduit 7e can be cleaned in the first drive state. The forceps plug pipe sleeve 2ba of the treatment instrument insertion port 2b can be cleaned, and clogging of the connection conduit 7c, the proximal end side conduit 7d, and the suction conduit 7e can be detected in the first drive state.

Note that when clogging is detected in the first drive state, the control section 11 displays a message or the like indicative of the clogging on, for example, a display apparatus not shown and stops the cleaning process.

(Second Drive State Execution Process: S2)

Figure 4:
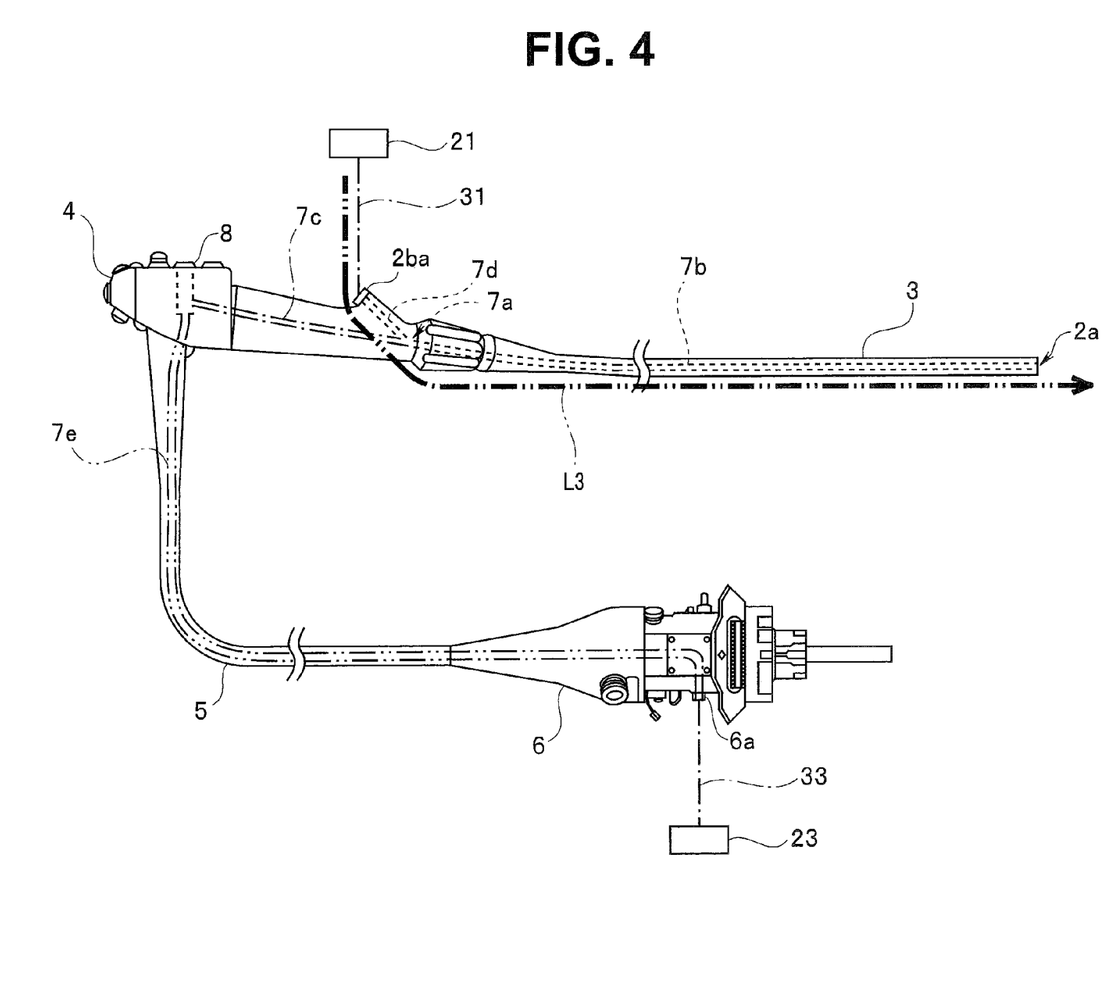
FIG. 4 is a diagram for describing a flow of the liquid in a second drive state execution process according to the embodiment of the present invention.

The second drive state execution process is a process of cleaning the conduit from the forceps plug pipe sleeve 2ba of the treatment instrument insertion port 2b to the opening 2a of the distal end portion of the insertion portion 3 and detecting clogging of the distal end side conduit 7b and the proximal end side conduit 7d.

The control section 11 executes the second drive state by controlling the electromagnetic valves 41 to 45 to turn off the electromagnetic valve 41, turn off the electromagnetic valve 42, turn on the electromagnetic valve 43, turn off the electromagnetic valve 44, and turn off the electromagnetic valve 45.

FIG. 4 is a diagram for describing a flow of the liquid in the second drive state execution process.

In the second drive state, the control section 11 controls the electromagnetic valves 41 to 45 as described above. As shown in FIG. 4, the liquid is supplied into the proximal end side conduit 7d of the connection conduit from the forceps plug pipe sleeve 2ba of the treatment instrument insertion port 2b, and the liquid is ejected from the opening 2a of the distal end portion of the insertion portion 3.

In the second drive state, the electromagnetic valve 41 is turned off and opened, and the liquid from the flow liquid pump 13 is supplied to the second cleaning tube 31. The electromagnetic valve 43 is turned on and closed, and the liquid from the flow liquid pump 13 is not supplied to the suction pipe sleeve 6a of the connector portion 6 through the first cleaning tube 33.

In the second drive state, the electromagnetic valve 42 is turned off and opened, and the passage between the forceps plug pipe sleeve 2ba of the treatment instrument insertion port 2b and the connector 31b enters the sealed state in which the liquid is not leaked. The electromagnetic valve 44 is turned off and opened, and the passage between the suction pipe sleeve 6a and the connector 33b enters the sealed state in which the liquid is not leaked. The electromagnetic valve 45 is turned off and opened, and the passage between the suction cylinder 8 and the connector 35b enters the sealed state in which the liquid is not leaked.

That is, the control section 11 controls the electromagnetic valves 41 to 45 and the flow liquid pump 13 to set the second drive state, in which the control section 11 controls the electromagnetic valve 44 to put the first cleaning tube 33 into the off-state, the control section 11 controls the electromagnetic valve 42 to put the second cleaning tube 31 into the off-state, the control section 11 controls the electromagnetic valve 45 to put the connector 35b into the off-state, the control section 11 sets the state in which the supply of the fluid from the flow liquid pump 13 to the first cleaning tube 33 is halted, and the control section 11 sets the state in which the fluid is supplied from the flow liquid pump 13 to the second cleaning tube 31.

As a result, the passage between the forceps plug pipe sleeve 2ba and the connector 31b enters the sealed state in the second drive state, and the entire amount of the liquid from the flow liquid pump 13 is poured into the proximal end side conduit 7d. The suction cylinder 8 and the suction pipe sleeve 6a are in the sealed state, and the entire amount of the liquid poured into the proximal end side conduit 7d is poured into the distal end side conduit 7b. The liquid poured into the distal end side conduit 7b is ejected from the opening 2a of the distal end portion of the insertion portion 3.

In the second drive state, the liquid poured into the proximal end side conduit 7d from the forceps plug pipe sleeve 2ba of the treatment instrument insertion port 2b flows in the proximal end side conduit 7d and the distal end side conduit 7b as indicated by an alternate long and two short dashes line in FIG. 4. However, the liquid flows only in the distal end side conduit 7b even if the inner diameter of the distal end side conduit 7b is small. Therefore, the speed of flow of the liquid flowing in the proximal end side conduit 7d is high, and the amount of flow is large. FIG. 4 illustrates that the amount of a flow L3 indicated by a thick alternate long and two short dashes line is large.

Therefore, the connectors 31b, 33b, and 35b are in the sealed state in the second drive state, and the entire amount of the liquid poured into the proximal end side conduit 7d from the forceps plug pipe sleeve 2ba of the treatment instrument insertion port 2b flows in the proximal end side conduit 7d and the distal end side conduit 7b at a high speed of flow. Thus, the inside of the proximal end side conduit 7d and the distal end side conduit 7b is cleaned.

Furthermore, when one of the proximal end side conduit 7d and the distal end side conduit 7b is clogged by foreign matters, the detection value of the flow amount sensor 17, that is, the fluid feeding amount becomes small, and the clogging can also be detected.

As described, the inside of the proximal end side conduit 7d and the distal end side conduit 7b can be cleaned, and clogging of the proximal end side conduit 7d and the distal end side conduit 7b can be detected in the second drive state.

Note that when clogging is detected in the second drive state, the control section 11 also displays a message or the like indicative of the clogging on, for example, a display apparatus not shown and stops the cleaning process.

(Third Drive State Execution Process: S3)

Figure 5:
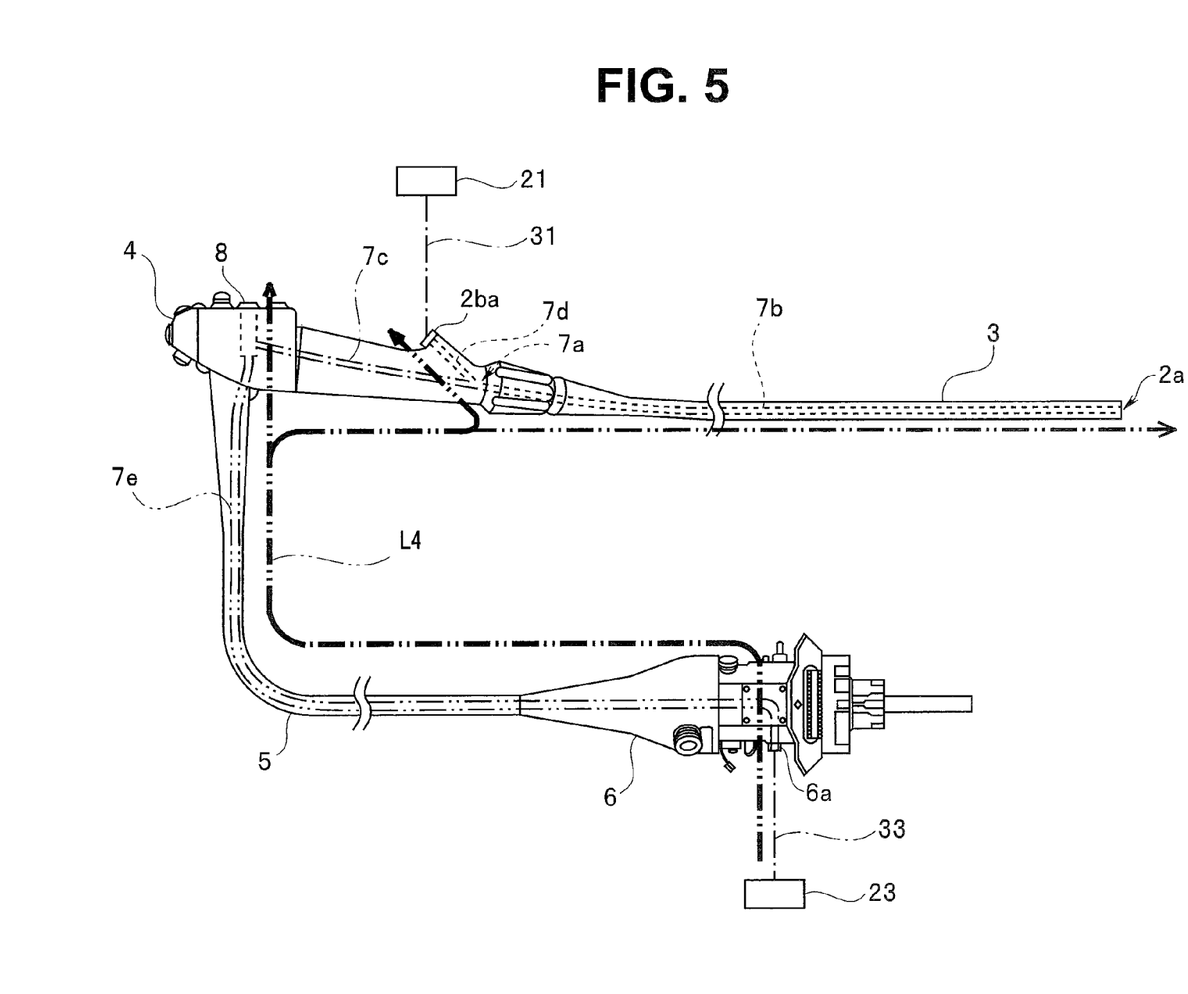
FIG. 5 is a diagram for describing a flow of the liquid in a third drive state execution process according to the embodiment of the present invention.

The third drive state execution process is a process of cleaning the suction pipe sleeve 6a, the forceps plug pipe sleeve 2ba of the treatment instrument insertion port 2b, and the suction cylinder 8.

The control section 11 executes the third drive state by controlling the electromagnetic valves 41 to 45 to turn on the electromagnetic valve 41, turn on the electromagnetic valve 42, turn off the electromagnetic valve 43, turn on the electromagnetic valve 44, and turn on the electromagnetic valve 45.

FIG. 5 is a diagram for describing a flow of the liquid in the third drive state execution process.

In the third drive state, the control section 11 controls the electromagnetic valves 41 to 45 as described above. As shown in FIG. 5, the liquid is supplied into the suction conduit 7e from the suction pipe sleeve 6a. The liquid is leaked out from between the suction pipe sleeve 6a and the connector 33b, between the suction cylinder 8 and the connector 35b, and between the forceps plug pipe sleeve 2ba of the treatment instrument insertion port 2b and the connector 31b. The liquid is ejected from the opening 2a of the distal end portion of the insertion portion 3.

In the third drive state, the electromagnetic valve 41 is turned on and closed, and the liquid from the flow liquid pump 13 is not supplied to the second cleaning tube 31. The electromagnetic valve 43 is turned off and opened, and the liquid from the flow liquid pump 13 is supplied to the suction pipe sleeve 6a of the connector portion 6 through the first cleaning tube 33.

In the third drive state, the electromagnetic valve 42 is turned on and closed, and the passage between the forceps plug pipe sleeve 2ba of the treatment instrument insertion port 2b and the connector 31b enters the unsealed state. The electromagnetic valve 44 is turned on and closed, and the passage between the suction pipe sleeve 6a and the connector 33b enters the unsealed state. The electromagnetic valve 45 is turned on and closed, and the passage between the suction cylinder 8 and the connector 35b enters the unsealed state.

That is, the control section 11 controls the electromagnetic valves 41 to 45 and the flow liquid pump 13 to set the third drive state, in which the control section 11 controls the electromagnetic valve 44 to put the first cleaning tube 33 into the on-state, the control section 11 controls the electromagnetic valve 42 to put the second cleaning tube 31 into the on-state, the control section 11 controls the electromagnetic valve 45 to put the connector 35b into the on-state, the control section 11 sets the state in which the fluid is supplied from the flow liquid pump 13 to the first cleaning tube 33, and the control section 11 sets the state in which the supply of the fluid from the flow liquid pump 13 to the second cleaning tube 31 is halted.

As a result, the passage between the suction pipe sleeve 6a and the connector 33b enters the unsealed state in the third drive state. The liquid from the flow liquid pump 13 is leaked from between the suction pipe sleeve 6a and the connector 33b and is poured into the suction conduit 7e. The liquid poured into the suction conduit 7e is leaked from between the suction cylinder 8 and the connector 35b and also poured into the connection conduit 7c, because the passage between the suction cylinder 8 and the connector 35b is in the unsealed state. The liquid poured into the connection conduit 7c is poured into the distal end side conduit 7b and the proximal end side conduit 7d.

The liquid poured into the distal end side conduit 7b is ejected from the opening 2a of the distal end portion of the insertion portion 3. The liquid poured into the proximal end side conduit 7d is also leaked out from between the forceps plug pipe sleeve 2ba and the connector 31b, because the passage between the forceps plug pipe sleeve 2ba of the treatment instrument insertion port 2b and the connector 31b is in the unsealed state.

In the third drive state, the liquid poured into the suction conduit 7e from the suction pipe sleeve 6a flows in the suction conduit 7e, the connection conduit 7c, the proximal end side conduit 7d, and the distal end side conduit 7b as indicated by an alternate long and two short dashes line L4 in FIG. 5. The liquid is leaked out from between the suction pipe sleeve 6a and the connector 33b, between the suction cylinder 8 and the connector 35b, and between the forceps plug pipe sleeve 2ba of the treatment instrument insertion port 2b and the connector 31b.

Therefore, in the third drive state, the suction pipe sleeve 6a, the suction cylinder 8, and the forceps plug pipe sleeve 2ba of the treatment instrument insertion port 2b can be cleaned by the liquid poured into the suction conduit 7e from the suction pipe sleeve 6a.

As described, the suction pipe sleeve 6a, the suction cylinder 8, and the forceps plug pipe sleeve 2ba of the treatment instrument insertion port 2b can be cleaned in the execution of the third drive state.

(Modification of Third Drive State)

The third drive state execution process S3 in FIG. 2 can be replaced by any one of fourth to sixth drive states described below.

Note that although the liquid is supplied from the suction pipe sleeve 6a in the third drive state, the liquid may be supplied from the forceps plug pipe sleeve 2ba of the treatment instrument insertion port 2b in a first modification, instead of the supply of the liquid from the suction pipe sleeve 6a. In this case, the control section 11 controls the electromagnetic valves 41 and 43 to turn off and open the electromagnetic valve 41 and turn on and close the electromagnetic valve 43.

That is, the control section 11 controls the electromagnetic valves 41 to 45 and the flow liquid pump 13 to set the third drive state, in which the control section 11 controls the electromagnetic valve 44 to put the first cleaning tube 33 into the on-state, the control section 11 controls the electromagnetic valve 42 to put the second cleaning tube 31 into the on-state, the control section 11 controls the electromagnetic valve 45 to put the connector 35b into the on-state, the control section 11 sets the state in which the supply of the fluid from the flow liquid pump 13 to the first cleaning tube 33 is halted, and the control section 11 sets the state in which the fluid is supplied from the flow liquid pump 13 to the second cleaning tube 31.

According to the fourth drive state of the first modification, the forceps plug pipe sleeve 2ba of the treatment instrument insertion port 2b, the suction pipe sleeve 6a, and the suction cylinder 8 can also be cleaned by the liquid poured into the proximal end side conduit 7d from the forceps plug pipe sleeve 2ba of the treatment instrument insertion port 2b.

Note that although the liquid is supplied from the suction pipe sleeve 6a in the third drive state, and the liquid is supplied from the forceps plug pipe sleeve 2ba of the treatment instrument insertion port 2b in the first modification, both of the supply of the liquid from the suction pipe sleeve 6a and the supply of the liquid from the forceps plug pipe sleeve 2ba of the treatment instrument insertion port 2b may be performed at the same time in a second modification.

In this case, the control section 11 controls the electromagnetic valves 41 and 43 to set the state, in which the control section 11 turns off and opens the electromagnetic valve 41, and the control section 11 turns off and opens the electromagnetic valve 43.

That is, the control section 11 controls the electromagnetic valves 41 to 45 and the flow liquid pump 13 to set the third drive state, in which the control section 11 controls the electromagnetic valve 44 to put the first cleaning tube 33 into the on-state, the control section 11 controls the electromagnetic valve 42 to put the second cleaning tube 31 into the on-state, the control section 11 controls the electromagnetic valve 45 to put the connector 35b into the on-state, the control section 11 sets the state in which the fluid is supplied from the flow liquid pump 13 to the first cleaning tube 33, and the control section 11 sets the state in which the fluid is supplied from the flow liquid pump 13 to the second cleaning tube 31.

According to the fifth drive state of the second modification, the suction pipe sleeve 6a, the suction cylinder 8, and the forceps plug pipe sleeve 2ba of the treatment instrument insertion port 2b can also be cleaned by the liquid poured into the suction conduit 7e from the suction pipe sleeve 6a and the liquid poured into the proximal end side conduit 7d from the forceps plug pipe sleeve 2ba of the treatment instrument insertion port 2b.

In the third drive state, the liquid is supplied from the suction pipe sleeve 6a. The liquid is supplied from the forceps plug pipe sleeve 2ba of the treatment instrument insertion port 2b in the first modification. Both of the supply of the liquid from the forceps plug pipe sleeve 2ba of the treatment instrument insertion port 2b and the supply of the liquid from the suction pipe sleeve 6a are performed in the third modification. However, the supply of the liquid from the suction pipe sleeve 6a and the supply of the liquid from the forceps plug pipe sleeve 2ba of the treatment instrument insertion port 2b may be alternately performed in a third modification. In this case, the control section 11 controls the electromagnetic valves 41 and 43 to alternately set the state in which the control section 11 turns on and closes the electromagnetic valve 41 and turns off and opens the electromagnetic valve 43 and the state in which the control section 11 turns off and opens the electromagnetic valve 41 and turns on and closes the electromagnetic valve 43.

That is, the control section 11 controls the electromagnetic valves 41 to 45 and the flow liquid pump 13 to set the third drive state, in which the control section 11 controls the electromagnetic valve 44 to put the first cleaning tube 33 into the on-state, the control section 11 controls the electromagnetic valve 42 to put the second cleaning tube 31 into the on-state, the control section 11 controls the electromagnetic valve 45 to put the connector 35b into the on-state, and the control section 11 alternately sets the state in which the fluid is supplied from the flow liquid pump 13 to the first cleaning tube 33 and the state in which the fluid is supplied from the flow liquid pump 13 to the second cleaning tube 31.

According to the sixth drive state of the third modification, the suction pipe sleeve 6a, the suction cylinder 8, and the forceps plug pipe sleeve 2ba of the treatment instrument insertion port 2b can be cleaned by the liquid poured into the suction conduit 7e from the suction pipe sleeve 6a and the liquid poured into the proximal end side conduit 7d from the forceps plug pipe sleeve 2ba of the treatment instrument insertion port 2b.

As described, the embodiment can provide an endoscope reprocessor that allows securing washability of a pipe sleeve part and detecting clogging of a conduit and that can obtain a value equal to or greater than a predetermined value for the speed of flow of a liquid flowing in the conduit to increase the washability in the conduit.

Particularly, an endoscope reprocessor that allows securing washability of a pipe sleeve part and detecting clogging of a conduit and that can obtain a value equal to or greater than a predetermined value for the speed of flow of a liquid flowing in the conduit to increase the washability in the conduit can be provided for an endoscope including a conduit inserted into an insertion portion with a small diameter.

According to the embodiment, a cleaning time period is also reduced as a result.

Note that although the supply of air is controlled to switch the two states, the sealed state and the unsealed state, in the connector that can switch the two states in the embodiment and the respective modifications, the two states may be switched by a method other the supply of air.

The present invention is not limited to the embodiments, and various changes, improvements, and the like can be made without changing the scope of the present invention.

What is claimed is:

1. An endoscope reprocessor comprising:
  a first connection connector to which a first cleaning tube is attached, the first cleaning tube being connected to a suction pipe sleeve of an endoscope and capable of being switched between a first sealed state in which an entire amount of a first fluid is introduced into the suction pipe sleeve and a first leak state in which the first fluid is introduced into the suction pipe sleeve and a first predetermined amount of the first fluid is leaked to an outer circumference of the suction pipe sleeve, wherein the first cleaning tube comprises a first connector supplied with a first air, the first connector entering the first sealed state by sealing a passage between the suction pipe sleeve and the first connector and entering the first leak state in which the first fluid is leaked from between the suction pipe sleeve and the first connector to the outer circumference by not sealing the passage between the suction pipe sleeve and the first connector;
  a first valve configured to control a supply of the first air so that the first connector is put into the first sealed state or the first fluid is leaked from between the suction pipe sleeve and the first connector to the outer circumference, to switch between the first leak state and the first sealed state of the first cleaning tube;
  a first pump configured to supply the first fluid from the first connection connector to the suction pipe sleeve through the first cleaning tube;
  a second connection connector to which a second cleaning tube is attached, the second cleaning tube being connected to a forceps plug pipe sleeve of the endoscope and capable of being switched between a second sealed state in which an entire amount of a second fluid is introduced into the forceps plug pipe sleeve and a second leak state in which the second fluid is introduced into the forceps plug pipe sleeve and a second predetermined amount of the second fluid is leaked to an outer circumference of the forceps plug pipe sleeve, wherein the second cleaning tube comprises a second connector supplied with a second air, the second connector entering the second sealed state by sealing a passage between the forceps plug pipe sleeve and the second connector and entering the second leak state in which the second fluid is leaked from between the forceps plug pipe sleeve and the second connector to the outer circumference by not sealing the passage between the forceps plug pipe sleeve and the second connector;

a second valve configured to control a supply of the second air so that the second connector is put into the second sealed state or the second fluid is leaked from between the forceps plug pipe sleeve and the second connector to the outer circumference, to switch between the second leak state and the second sealed state of the second cleaning tube;

a second pump configured to supply the second fluid from the second connection connector to the forceps plug pipe sleeve through the second cleaning tube;

a third valve configured to control a supply of a third air to switch a third sealed state and a third leak state of a third connector plugging a suction cylinder of the endoscope, wherein a third fluid is not leaked from the suction cylinder in the third sealed state, and a third predetermined amount of the third fluid is leaked from the suction cylinder in the third leak state; and a controller configured to control the first valve, the second valve, the third valve, the first pump, and the second pump to set a first drive state, in which the controller controls the first valve to put the first cleaning tube into the first sealed state, the controller controls the second valve to put the second cleaning tube into the second leak state, the controller controls the third valve to put the third connector into the third sealed state, the controller sets a state in which the first fluid is supplied from the first pump to the first cleaning tube, and the controller sets a state in which supply of the second fluid from the second pump to the second cleaning tube is halted.

2. The endoscope reprocessor according to claim 1, wherein the controller controls the first valve, the second valve, the third valve, the first pump, and the second pump to set a second drive state, in which the controller controls the first valve to put the first cleaning tube into the first sealed state, the controller controls the second valve to put the second cleaning tube into the second sealed state, the controller controls the third valve to put the third connector into the third sealed state, the controller sets a state in which the supply of the first fluid from the first pump to the first cleaning tube is halted, and the controller sets a state in which the second fluid is supplied from the second pump to the second cleaning tube.

3. The endoscope reprocessor according to claim 1, wherein the controller controls the first valve, the second valve, the third valve, the first pump, and the second pump to set a third drive state, in which the controller controls the first valve to put the first cleaning tube into the first leak state, the controller controls the second valve to put the second cleaning tube into the second leak state, the controller controls the third valve to put the third connector into the third leak state, the controller sets the state in which the first fluid is supplied from the first pump to the first cleaning tube, and the controller sets the state in which the supply of the second fluid from the second pump to the second cleaning tube is halted.

4. The endoscope reprocessor according to claim 1, wherein the controller controls the first valve, the second valve, the third valve, the first pump, and the second pump to set a fourth drive state, in which the controller controls the first valve to put the first cleaning tube into the first leak state, the controller controls the second valve to put the second cleaning tube into the second leak state, the controller controls the third valve to put the third connector into the third leak state, the controller sets the state in which the supply of the first fluid from the first pump to the first cleaning tube is halted, and the controller sets the state in which the second fluid is supplied from the second pump to the second cleaning tube.

5. The endoscope reprocessor according to claim 1, wherein the controller controls the first valve, the second valve, the third valve, the first pump, and the second pump to set a fifth drive state, in which the controller controls the first valve to put the first cleaning tube into the first leak state, the controller controls the second valve to put the second cleaning tube into the second leak state, the controller controls the third valve to put the third connector into the third leak state, the controller sets the state in which the first fluid is supplied from the first pump to the first cleaning tube, and the controller sets the state in which the second fluid is supplied from the second pump to the second cleaning tube.

6. The endoscope reprocessor according to claim 1, wherein the controller controls the first valve, the second valve, the third valve, the first pump, and the second pump to set a sixth drive state, in which the controller controls the first valve to put the first cleaning tube into the first leak state, the controller controls the second valve to put the second cleaning tube into the second leak state, the controller controls the third valve to put the third connector into the third leak state, and the controller alternately sets the state in which the first fluid is supplied from the first pump to the first cleaning tube and the state in which the second fluid is supplied from the second pump to the second cleaning tube.

7. The endoscope reprocessor according to claim 1, further comprising a fourth valve configured to switch a state in which the first fluid is introduced from the first pump to the first cleaning tube and a state in which the first fluid is not introduced from the first pump to the first cleaning tube, wherein the controller controls the fourth valve to set the state in which the first fluid is supplied from the first pump to the first cleaning tube.

8. The endoscope reprocessor according to claim 1, further comprising a fifth valve configured to switch a state in which the second fluid is introduced from the second pump to the second cleaning tube and a state in which the second fluid is not introduced from the second pump to the second cleaning tube, wherein
the controller controls the fifth valve to set the state in which the supply of the second fluid from the second pump to the second cleaning tube is halted.

9. The endoscope reprocessor according to claim 1, further comprising
a flow amount sensor configured to measure an amount of flow of the first fluid and the second fluid supplied from the first pump and the second pump.

* * * * *